(12) United States Patent
Johnston

(10) Patent No.: US 8,588,922 B1
(45) Date of Patent: Nov. 19, 2013

(54) METHODS AND SYSTEMS FOR PRESENTING AUDIBLE CUES TO ASSIST IN FITTING A BILATERAL COCHLEAR IMPLANT PATIENT

(75) Inventor: Jacob Johnston, Winnetka, CA (US)

(73) Assignee: Advanced Bionics AG, Zug (CH)

( * ) Notice: Subject to any disclaimer, the term of this patent is extended or adjusted under 35 U.S.C. 154(b) by 621 days.

(21) Appl. No.: 12/847,091

(22) Filed: Jul. 30, 2010

(51) Int. Cl.
 *A61F 11/04* (2006.01)
(52) U.S. Cl.
 USPC .............................................. 607/57; 607/56
(58) Field of Classification Search
 USPC ...................................... 607/57, 59
 See application file for complete search history.

(56) References Cited

U.S. PATENT DOCUMENTS

| | | | | |
|---|---|---|---|---|
| 5,479,522 A * | 12/1995 | Lindemann et al. | ......... | 381/23.1 |
| 5,991,419 A * | 11/1999 | Brander | ......... | 381/312 |
| 6,839,447 B2 * | 1/2005 | Nielsen et al. | ......... | 381/312 |
| 2004/0202340 A1 * | 10/2004 | Armstrong et al. | ......... | 381/312 |
| 2006/0100672 A1 * | 5/2006 | Litvak | ......... | 607/57 |
| 2009/0030484 A1 * | 1/2009 | Chambers | ......... | 607/57 |

\* cited by examiner

*Primary Examiner* — Carl H Layno
*Assistant Examiner* — Jennifer Ghand
(74) *Attorney, Agent, or Firm* — ALG Intellectual Property, LLC

(57) ABSTRACT

An exemplary method of fitting a bilateral cochlear implant patient includes a fitting subsystem directing a first cochlear implant associated with a right ear of a bilateral cochlear implant patient to present a first set of one or more stimulation pulses to the patient and a second cochlear implant associated with a left ear of the patient to present a second set of one or more stimulation pulses to the patient, presenting a first audible cue during the presentation of each stimulation pulse included in the first set of one or more stimulation pulses, and presenting a second audible cue having one or more different acoustic properties than the first audible cue during the presentation of each stimulation pulse included in the second set of one or more stimulation pulses. Corresponding methods and systems are also described.

20 Claims, 11 Drawing Sheets

METHODS AND SYSTEMS FOR PRESENTING AUDIBLE CUES TO ASSIST IN FITTING A BILATERAL COCHLEAR IMPLANT PATIENT

BACKGROUND INFORMATION

The natural sense of hearing in human beings involves the use of hair cells in the cochlea that convert or transduce acoustic signals into auditory nerve impulses. Hearing loss, which may be due to many different causes, is generally of two types: conductive and sensorineural. Conductive hearing loss occurs when the normal mechanical pathways for sound to reach the hair cells in the cochlea are impeded. These sound pathways may be impeded, for example, by damage to the auditory ossicles. Conductive hearing loss may often be overcome through the use of conventional hearing aids that amplify sound so that acoustic signals can reach the hair cells within the cochlea. Some types of conductive hearing loss may also be treated by surgical procedures.

Sensorineural hearing loss, on the other hand, is caused by the absence or destruction of the hair cells in the cochlea, which are needed to transduce acoustic signals into auditory nerve impulses. People who suffer from sensorineural hearing loss may be unable to derive significant benefit from conventional hearing aid systems, no matter how loud the acoustic stimulus. This is because the mechanism for transducing sound energy into auditory nerve impulses has been damaged. Thus, in the absence of properly functioning hair cells, auditory nerve impulses cannot be generated directly from sounds.

To overcome sensorineural hearing loss, numerous cochlear implant systems—or cochlear prostheses—have been developed. Cochlear implant systems bypass the hair cells in the cochlea by presenting electrical stimulation directly to the auditory nerve fibers by way of one or more channels formed by an array of electrodes implanted in the cochlea. Direct stimulation of the auditory nerve fibers leads to the perception of sound in the brain and at least partial restoration of hearing function.

When a cochlear implant system is initially implanted in a patient, and during follow-up tests and checkups thereafter, it is usually necessary to "fit" the cochlear implant system to the patient. Fitting of a cochlear implant system to a patient is typically performed by an audiologist or the like who presents stimulation pulses to the patient and relies on verbal feedback from the patient as to how such stimulation pulses are perceived. Adjustments to the stimulation pulses may be made in response to the verbal feedback.

In addition to verbal feedback from the patient, the audiologist may look for non-verbal feedback provided by the patient, such as changes in facial expression, that may be indicative of a response of the patient to the applied stimulation pulses. Non-verbal feedback is especially important in pediatric fittings or in other situations in which verbal feedback is unavailable. However, when fitting a bilateral cochlear implant patient (i.e., a patient who has a separate cochlear implant for each ear), it is often difficult for the audiologist to know which cochlear implant elicits such non-verbal feedback.

SUMMARY

An exemplary method of fitting a bilateral cochlear implant patient includes a fitting subsystem 1) directing a first cochlear implant associated with a right ear of a bilateral cochlear implant patient to present a first set of one or more stimulation pulses to the patient and a second cochlear implant associated with a left ear of the patient to present a second set of one or more stimulation pulses to the patient, 2) presenting a first audible cue during the presentation of each stimulation pulse included in the first set of one or more stimulation pulses, and 3) presenting a second audible cue having one or more different acoustic properties than the first audible cue during the presentation of each stimulation pulse included in the second set of one or more stimulation pulses.

Another exemplary method of fitting a bilateral cochlear implant patient includes a fitting subsystem 1) directing a first cochlear implant associated with a first ear of a bilateral cochlear implant patient to present a first stimulation pulse to the patient, 2) presenting a first audible cue having a first pitch during the presentation of the first stimulation pulse, 3) directing a second cochlear implant associated with a second ear of the patient to present a second stimulation pulse to the patient subsequent to the presentation of the first stimulation pulse, and 4) presenting a second audible cue having a second pitch different than the first pitch during the presentation of the second stimulation pulse.

A system for fitting a bilateral cochlear implant patient includes a fitting facility and an audio presentation facility communicatively coupled to one another. The fitting facility is configured to direct a first cochlear implant associated with a right ear of a bilateral cochlear implant patient to present a first set of one or more stimulation pulses to the patient and a second cochlear implant associated with a left ear of the patient to present a second set of one or more stimulation pulses to the patient. The audio presentation facility is configured to present a first audible cue during the presentation of each stimulation pulse included in the first set of one or more stimulation pulses and present a second audible cue having one or more different acoustic properties than the first audible cue during the presentation of each stimulation pulse included in the second set of one or more stimulation pulses.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Methods and systems for presenting audible cues to assist in fitting a bilateral cochlear implant patient are described herein.

As described in more detail below, a fitting subsystem may be configured to direct a first cochlear implant associated with a right ear of a bilateral cochlear implant patient to present a first set of one or more stimulation pulses to the patient and a second cochlear implant associated with a left ear of the patient to present a second set of one or more stimulation pulses to the patient. The fitting subsystem may be further configured to present a first audible cue during the presentation of each stimulation pulse included in the first set of one or more stimulation pulses and present a second audible cue having one or more different acoustic properties than the first audible cue during the presentation of each stimulation pulse included in the second set of one or more stimulation pulses. As used herein, an "audible cue" refers to a tone or other sound that may be heard by a user of a fitting subsystem used to fit a bilateral cochlear implant patient. An audible cue may have any of a number of different acoustic properties, as will be described in more detail below.

Numerous advantages may be associated with the methods and systems described herein. For example, an audiologist using the fitting subsystem described herein may audibly recognize when each stimulation pulse included in the first and second sets of one or more stimulation pulses is presented to the patient by listening for the audible cues. Because the first and second audible cues are audibly distinguishable one from another, the audiologist may also recognize the source of each stimulation pulse (e.g., whether the stimulation pulse is presented by the first or second cochlear implant). This allows the audiologist to focus on non-verbal and other types of feedback that the patient may provide in response to the presentation of the stimulation pulses.

Figure 1:
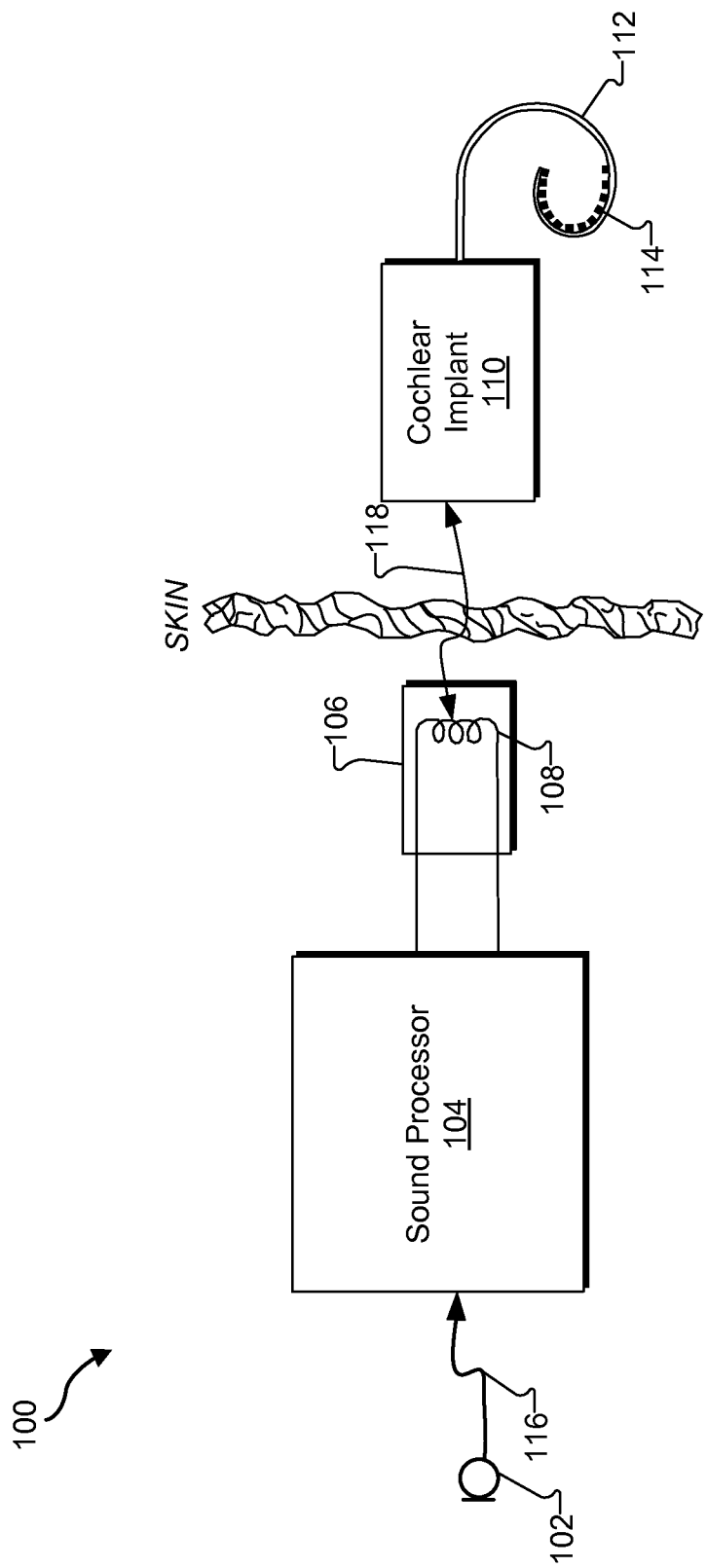
FIG. 1 illustrates an exemplary cochlear implant system according to principles described herein.

To facilitate an understanding of the methods and systems described herein, an exemplary cochlear implant system 100 will be described in connection with FIG. 1. As shown in FIG. 1, cochlear implant system 100 may include a microphone 102, a sound processor 104, a headpiece 106 having a coil 108 disposed therein, a cochlear implant 110 (also referred to as an "implantable cochlear stimulator"), and a lead 112 with a plurality of electrodes 114 disposed thereon. Additional or alternative components may be included within cochlear implant system 100 as may serve a particular implementation.

As shown in FIG. 1, microphone 102, sound processor 104, and headpiece 106 may be located external to a cochlear implant patient. In some alternative examples, microphone 102 and/or sound processor 104 may be implanted within the patient. In such configurations, the need for headpiece 106 may be obviated.

Microphone 102 may detect an audio signal and convert the detected signal to a corresponding electrical signal. The electrical signal may be sent from microphone 102 to sound processor 104 via a communication link 116, which may include a telemetry link, a wire, and/or any other suitable communication link.

Sound processor 104 is configured to direct cochlear implant 110 to generate and apply electrical stimulation (also referred to herein as "stimulation current") to one or more stimulation sites within a cochlea of the patient. To this end, sound processor 104 may process the audio signal detected by microphone 102 in accordance with a selected sound processing strategy to generate appropriate stimulation parameters for controlling cochlear implant 110. Sound processor 104 may include or be implemented by a behind-the-ear ("BTE") unit, a portable speech processor ("PSP"), and/or any other sound-processing unit as may serve a particular implementation. Exemplary components of sound processor 104 will be described in more detail below.

Sound processor 104 may be configured to transcutaneously transmit, in accordance with a sound processing program associated with cochlear implant 110, one or more control parameters and/or one or more power signals to cochlear implant 110 with coil 108 by way of a communication link 118. These control parameters may be configured to specify one or more stimulation parameters, operating parameters, and/or any other parameter by which cochlear implant 110 is to operate as may serve a particular implementation. Exemplary control parameters include, but are not limited to, stimulation current levels, volume control parameters, program selection parameters, operational state parameters (e.g., parameters that turn a sound processor and/or a cochlear implant on or off), audio input source selection parameters, fitting parameters, noise reduction parameters, microphone sensitivity parameters, microphone direction parameters, pitch parameters, timbre parameters, sound quality parameters, most comfortable current levels ("M levels"), threshold current levels ("T levels"), channel acoustic gain parameters, front and backend dynamic range parameters, current steering parameters, pulse rate values, pulse width values, frequency parameters, amplitude parameters, waveform parameters, electrode polarity parameters (i.e., anode-cathode assignment), location parameters (i.e., which electrode pair or electrode group receives the stimulation current), stimulation type parameters (i.e., monopolar, bipolar, or tripolar stimulation), burst pattern parameters (e.g., burst on time and burst off time), duty cycle parameters, spectral tilt parameters, filter parameters, and dynamic compression parameters. Sound processor 104 may also be configured to operate in accordance with one or more of the control parameters.

As shown in FIG. 1, coil 108 may be housed within headpiece 106, which may be affixed to a patient's head and positioned such that coil 108 is communicatively coupled to a corresponding coil included within cochlear implant 110. In this manner, control parameters and power signals may be wirelessly transmitted between sound processor 104 and cochlear implant 110 via communication link 118. It will be understood that data communication link 118 may include a bi-directional communication link and/or one or more dedicated uni-directional communication links. In some alternative embodiments, sound processor 104 and cochlear implant 110 may be directly connected with one or more wires or the like.

Cochlear implant 110 may be configured to generate electrical stimulation representative of an audio signal detected by microphone 102 in accordance with one or more stimulation parameters transmitted thereto by sound processor 104. Cochlear implant 110 may be further configured to apply the electrical stimulation to one or more stimulation sites within the cochlea via one or more electrodes 114 disposed along lead 112. In some examples, cochlear implant 110 may include a plurality of independent current sources each associated with a channel defined by one or more of electrodes 114. In this manner, different stimulation current levels may be applied to multiple stimulation sites simultaneously by way of multiple electrodes 114. In such examples, cochlear implant system 100 may be referred to as a "multi-channel cochlear implant system."

To facilitate application of the electrical stimulation generated by cochlear implant 110, lead 112 may be inserted within a duct of the cochlea such that electrodes 114 are in communication with one or more stimulation sites within the cochlea. As used herein, the term "in communication with" refers to electrodes 114 being adjacent to, in the general vicinity of, in close proximity to, directly next to, or directly on the stimulation site. Any number of electrodes 114 (e.g., sixteen) may be disposed on lead 112 as may serve a particular implementation.

Figure 2:
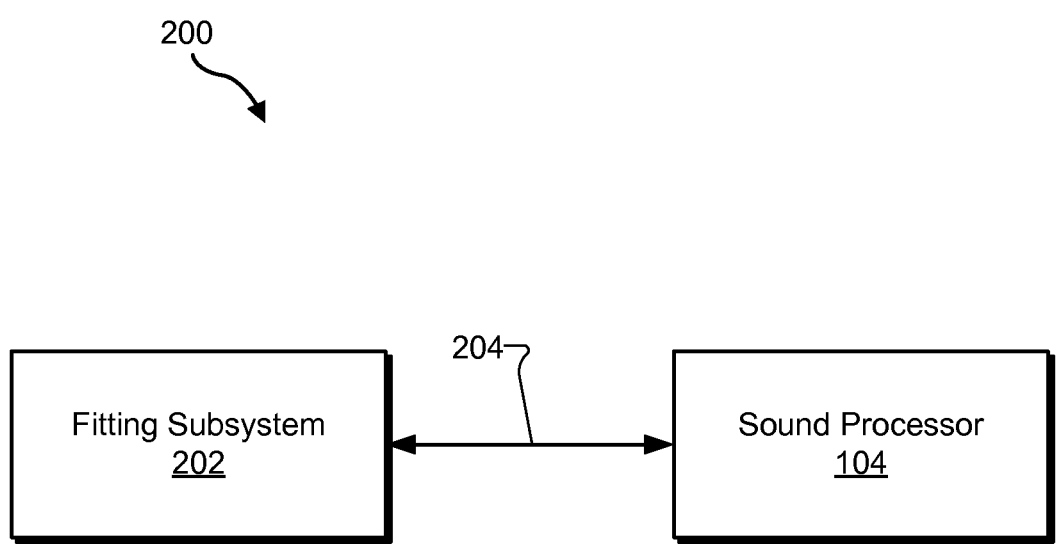
FIG. 2 illustrates an exemplary cochlear implant fitting system according to principles described herein.

FIG. 2 illustrates an exemplary cochlear implant fitting system 200 (or simply "fitting system 200") that may be used to fit a cochlear implant patient. As used herein, the terms "fitting a cochlear implant patient" and "fitting a cochlear implant to a patient" will be used interchangeably to refer to performing one or more fitting operations associated with sound processor 104, cochlear implant 110, and/or any other component of cochlear implant system 100 in order to optimize performance of cochlear implant system 100 for the patient. Such fitting operations may include, but are not limited to, adjusting one or more control parameters by which sound processor 104 and/or cochlear implant 110 operate, measuring one or more electrode impedances, performing one or more neural response detection operations, and/or performing one or more diagnostics procedures associated with the cochlear implant system.

As shown in FIG. 2, fitting system 200 may include a fitting subsystem 202 configured to be selectively and communicatively coupled to sound processor 104 of cochlear implant system 100 by way of a communication link 204. Fitting subsystem 202 and sound processor 104 may communicate using any suitable communication technologies, devices, networks, media, and protocols supportive of data communications.

Fitting subsystem 202 may be configured to perform one or more of the fitting operations described herein. To this end, fitting subsystem 202 may be implemented by any suitable combination of computing and communication devices including, but not limited to, a fitting station, a personal computer, a laptop computer, a handheld device, a mobile device (e.g., a mobile phone), a clinician's programming interface ("CPI") device, and/or any other suitable component as may serve a particular implementation. An exemplary implementation of fitting subsystem 202 will be described in more detail below.

Figure 3:
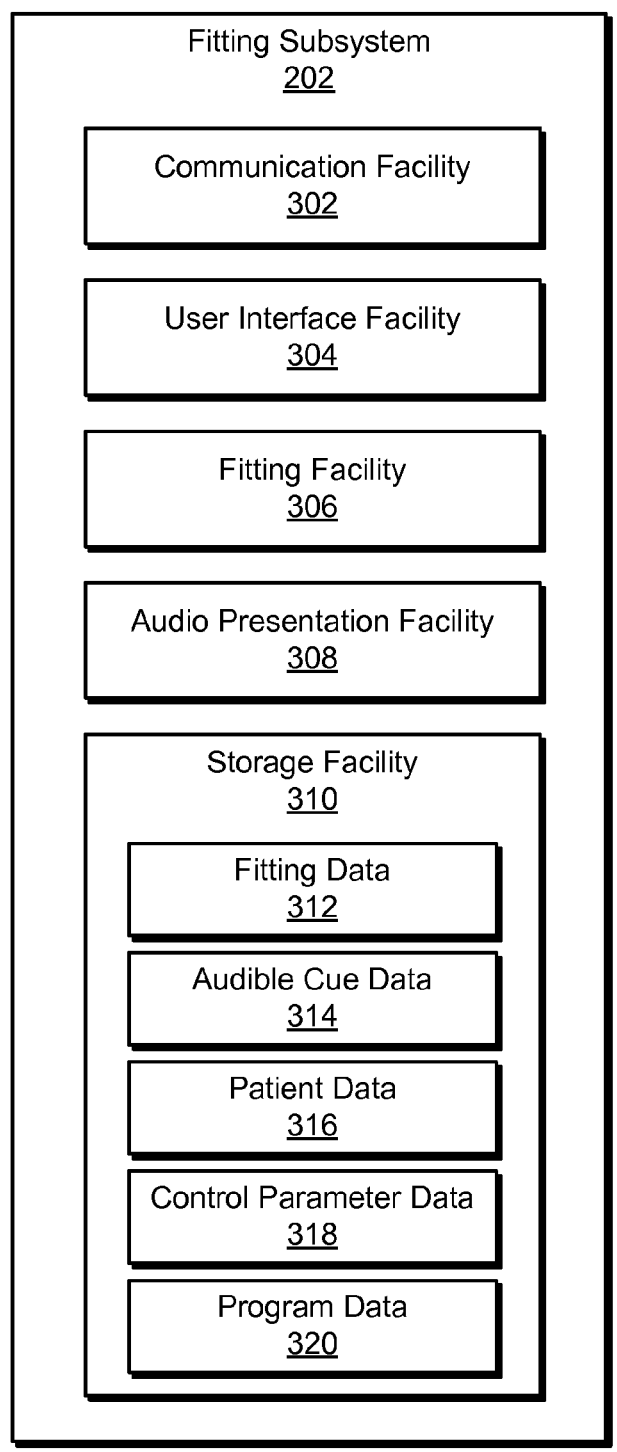
FIG. 3 illustrates exemplary components of an exemplary fitting subsystem according to principles described herein.

FIG. 3 illustrates exemplary components of fitting subsystem 202. As shown in FIG. 3, fitting subsystem 202 may include a communication facility 302, a user interface facility 304, a fitting facility 306, an audio presentation facility 308, and a storage facility 310, which may be communicatively coupled to one another using any suitable communication technologies. Each of these facilities will now be described in more detail.

Communication facility 302 may be configured to facilitate communication between fitting subsystem 202 and cochlear implant system 100 (e.g., sound processor 104 and/or cochlear implant 110). For example, communication facility 302 may be implemented by a CPI device, which may include any suitable combination of components configured to allow fitting subsystem 202 to interface and communicate with sound processor 104. Communication facility 302 may additionally or alternatively include one or more transceiver components configured to wirelessly transmit data (e.g., program data and/or control parameter data) to sound processor 104 and/or wirelessly receive data (e.g., feedback data, impedance measurement data, neural response data, etc.) from sound processor 104.

In some examples (e.g., during a fitting of a bilateral cochlear implant patient), communication facility 302 may facilitate selective and/or concurrent communication between multiple sound processors (e.g., right and left sound processors). In this manner, communication facility 302 may be configured to communicate with a first cochlear implant associated with a first ear (e.g., the right ear) of the patient by way of a first sound processor and a second cochlear implant associated with a second ear (e.g., the left ear) of the patient by way of a second sound processor.

Communication facility 302 may additionally or alternatively be configured to facilitate communication between fitting subsystem 202 and one or more other devices. For example, communication facility 302 may be configured to facilitate communication between fitting subsystem 202 and one or more computing devices (e.g., by way of the Internet and/or one or more other types of networks), reference implants, and/or any other computing device as may serve a particular implementation.

User interface facility 304 may be configured to provide one or more user interfaces configured to facilitate user interaction with fitting subsystem 202. For example, user interface facility 304 may provide a graphical user interface ("GUI") through which one or more functions, options, features, and/or tools associated with one or more fitting operations described herein may be provided to a user and through which user input may be received. In certain embodiments, user interface facility 304 may be configured to provide the GUI to a display device (e.g., a computer monitor) for display. In some examples, user interface facility 304 may be configured to provide a graphical user interface configured to graphically indicate a presentation of one or more sets of stimulation pulses to a bilateral cochlear implant patient, as will be described in more detail below.

Fitting facility 306 may be configured to perform one or more fitting operations. For example, fitting facility 306 may be configured to adjust one or more control parameters by which sound processor 104 and/or cochlear implant 110 operate, direct sound processor 104 to measure one or more electrode impedances, perform one or more neural response detection operations, and/or perform one or more diagnostics procedures associated with cochlear implant system 100.

In some examples, fitting facility 306 may direct a first cochlear implant associated with a right ear of a bilateral cochlear implant patient to present a first set of one or more stimulation pulses to the patient and a second cochlear implant associated with a left ear of the patient to present a second set of one or more stimulation pulses to the patient. The first and second sets of stimulation pulses may be presented in any suitable order. For example, one or more stimulation pulses may be alternatingly applied by the first and second cochlear implants, concurrently applied by the first and second cochlear implants, and/or in any other manner as may serve a particular implementation. A user of fitting subsystem 202 may adjust one or more parameters associated with the stimulation pulses (e.g., amplitude levels, etc.) in response to patient feedback, which may be verbal and/or non-verbal.

Audio presentation facility 308 may be configured to provide one or more audible cues configured to coincide with a presentation of one or more stimulation pulses to a cochlear implant patient. In this manner, as will be described in more detail below, a user of fitting subsystem 202 may know exactly when each of the one or more stimulation pulses is presented to the patient without having to look at a display screen of fitting subsystem 202. This allows the user to focus on non-verbal feedback that the patient may provide in response to the presentation of the one or more stimulation pulses.

In configurations wherein fitting subsystem 202 is used to fit a bilateral cochlear implant patient, audio presentation facility 308 may present audible cues that are configured to acoustically represent which of the two cochlear implants is presenting the stimulation pulses. For example, audio presentation facility 308 may present a first audible cue each time a first cochlear implant associated with the right ear of a patient presents a stimulation pulse and a second audible cue each time a second cochlear implant associated with the left ear of a patient presents a stimulation pulse. The first and second audible cues may be audibly distinct one from another (i.e., have distinct sets of acoustic properties). For example, the first and second audible cues may have distinct pitches, volume levels, patterns (e.g., the first audible cue may include a first number of beeps (e.g., three beeps) or a chirp signal that increases in pitch over time while the second audible cue may include a second number of beeps (e.g., two beeps) or a chirp signal that decreases in pitch over time), and/or any other audibly distinguishable characteristic.

In some examples, the first and second audible cues may be presented concurrently to represent concurrent presentation of stimulation pulses performed by the first and second cochlear implants. The concurrent presentation of the first and second audible cues may result in the first and second audible cues mixing to form a third audible cue having a distinct set of acoustic properties. For example, the first and second audible cues may have different pitches that, when presented concurrently, result in a mixed audible cue that has a pitch equivalent to a combination of the first and second pitches. In this manner, a user of fitting subsystem 202 may recognize instances of concurrent stimulation performed by the first and second cochlear implants by listening for the mixed audible cue.

Audio presentation facility 308 may be configured to dynamically adjust one or more acoustic properties of an audible cue in accordance with a change in stimulation level of one or more stimulation pulses included in a set of one or more stimulation pulses. For example, a user of fitting subsystem 202 may increase a stimulation level of stimulation pulses being presented to a patient by way of a cochlear implant patient. In response, audio presentation facility 308 may dynamically increase the pitch of the audible cue used to represent the presentation of the stimulation pulses. Audio presentation facility 308 may alternatively adjust any other acoustic property of the audible cue as may serve a particular implementation.

In some examples, an audible cue is synchronized with a corresponding stimulation pulse. In other words, the audible cue begins when the stimulation pulse begins and ends when the stimulation pulse ends. In this manner, a user of fitting subsystem 202 may know when the stimulation pulse starts and stops by noting when the stimulation pulse's corresponding audible cue starts and stops.

Audio presentation facility 308 may be implemented by any suitable combination of audio processing and presentation components as may serve a particular implementation. For example, audio presentation facility 308 may be implemented by one or more computing devices, signal processors, and/or speakers.

Storage facility 310 may be configured to maintain fitting data 312 associated with one or more fitting operations, audible cue data 314 representative of one or more acoustic properties of audible cues presented by audio presentation facility 308, patient data 316 representative of data descriptive of or otherwise associated with one or more cochlear implant patients, control parameter data 318 representative of one or more control parameters, and program data 320 representative of one or more sound processing programs, any or all of which may be maintained within one or more data sets. Storage facility 310 may be configured to maintain additional or alternative data as may serve a particular implementation.

Figure 4:
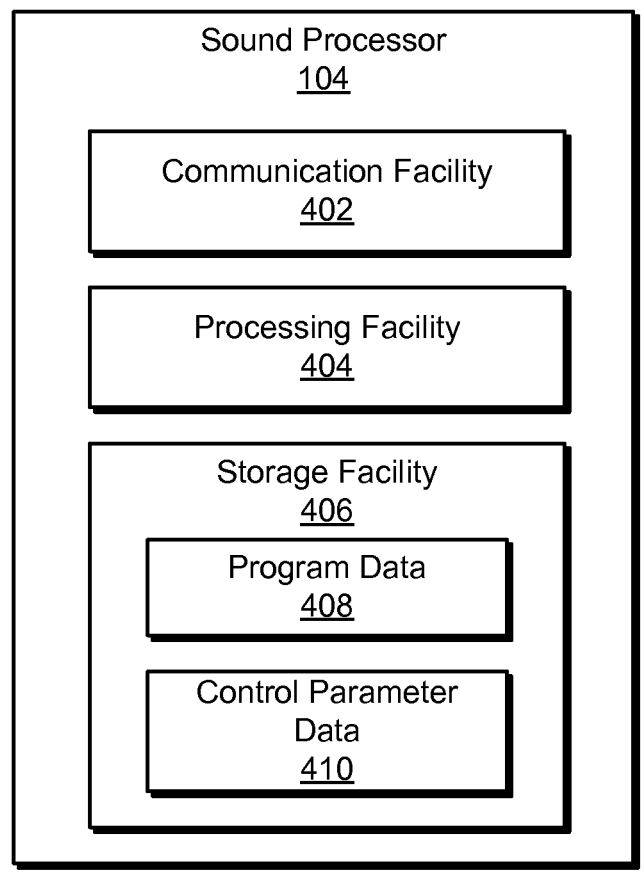
FIG. 4 illustrates exemplary components of a sound processor according to principles described herein.

FIG. 4 illustrates exemplary components of sound processor 104. As shown in FIG. 4, sound processor 104 may include a communication facility 402, a processing facility 404, and a storage facility 406, any or all of which may be in communication with one another using any suitable communication technologies. Each of these facilities will now be described in more detail.

Communication facility 402 may be configured to facilitate communication between sound processor 104 and fitting subsystem 202. For example, communication facility 402 may be configured to facilitate electrical coupling of sound processor 104 to a CPI device in order to communicate with fitting subsystem 202. Communication facility 402 may be further configured to facilitate communication between sound processor 104 and cochlear implant 110. For example, communication facility 402 may include transceiver components configured to wirelessly transmit data (e.g., control parameters and/or power signals) to cochlear implant 110 and/or wirelessly receive data from cochlear implant 110.

Processing facility 404 may be configured to perform one or more signal processing heuristics on an audio signal presented to the patient. For example, processing facility 404 may perform one or more pre-processing operations, spectral analysis operations, noise reduction operations, mapping operations, and/or any other types of signal processing operations on a detected audio signal as may serve a particular implementation. In some examples, processing facility 404 may generate and/or adjust one or more control parameters governing an operation of cochlear implant 110 (e.g., one or more stimulation parameters defining the stimulation pulses to be generated and applied by cochlear implant 110). In some examples, processing facility 404 may be configured to operate in accordance with one or more sound processing programs provided by fitting subsystem 202 and/or otherwise stored within storage facility 406.

Storage facility 406 may be configured to maintain program data 408 representative of one or more sound processing programs and control parameter data 410 representative of one or more control parameters. Storage facility 406 may be configured to maintain additional or alternative data as may serve a particular implementation.

Figure 5:
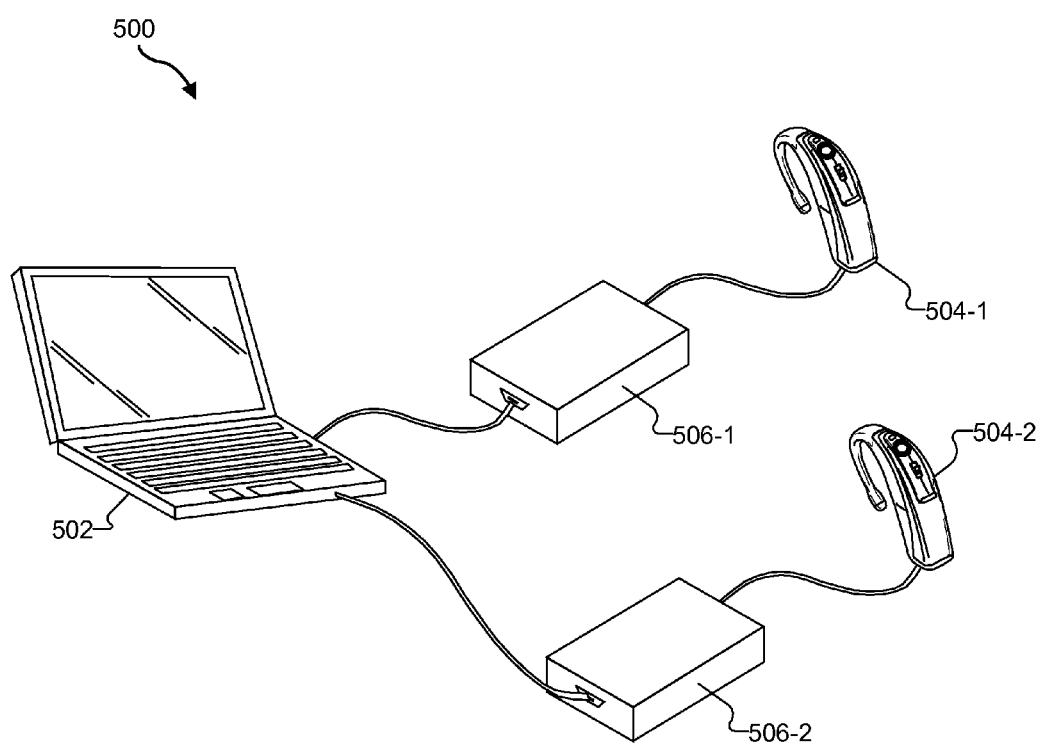
FIG. 5 illustrates an exemplary implementation of the cochlear implant fitting system of FIG. 2 according to principles described herein.

FIG. 5 illustrates an exemplary implementation 500 of fitting system 200 that may be used to fit a bilateral cochlear implant patient. In implementation 500, a fitting station 502 may be selectively and communicatively coupled to first and second BTE units 504-1 and 504-2 (collectively referred to herein as "BTE units 504") by way of corresponding CPI devices 506-1 and 506-2 (collectively referred to herein as "CPI devices 506"). BTE unit 504-1 may be associated with a first cochlear implant (e.g., a cochlear implant associated with a right ear of a patient) and BTE unit 504-2 may be associated with a second cochlear implant (e.g., a cochlear implant associated with a left ear of the patient). BTE units 504 are merely exemplary of the many different types of sound processors that may be used in accordance with the systems and methods described herein. Fitting station 502 may be selectively and communicatively coupled to any other type of sound processor as may serve a particular implementation.

Fitting station 502 may include any suitable computing device and/or combination of computing devices and be configured to perform one or more of the fitting operations described herein. For example, fitting station 502 may display one or more GUIs configured to facilitate selection of one or more measurements to perform using BTE units 504, selection of one or more sound processing programs by which BTE units 504 operate, adjustment of one or more control parameters by which BTE units 504 operate, and/or any other fitting operation as may serve a particular implementation.

CPI devices 506 may be configured to facilitate communication between fitting station 502 and BTE units 504. In some examples, CPI devices 506 may be selectively and communicatively coupled to fitting station 502 and/or BTE units 504 by way of one or more ports included within fitting station 502 and BTE units 504.

Figure 6:
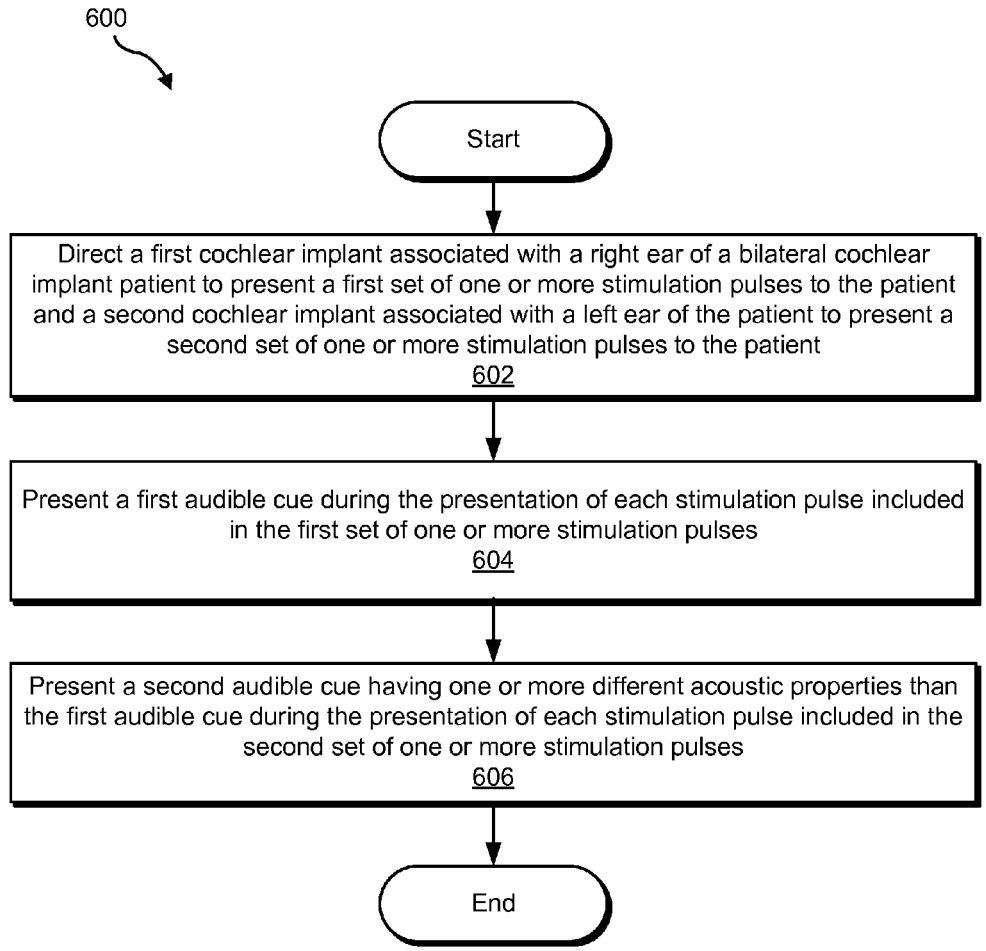
FIG. 6 illustrates an exemplary method of presenting audible cues to assist in fitting a bilateral cochlear implant patient according to principles described herein.

FIG. 6 illustrates an exemplary method 600 of presenting audible cues to assist in fitting a bilateral cochlear implant patient. While FIG. 6 illustrates exemplary steps according to one embodiment, other embodiments may omit, add to, reorder, and/or modify any of the steps shown in FIG. 6. One or more of the steps shown in FIG. 6 may be performed by any component or combination of components of fitting subsystem 202 and/or fitting station 502.

In step 602, a first cochlear implant associated with a right ear of a bilateral cochlear implant patient is directed to present a first set of one or more stimulation pulses to the patient and a second cochlear implant associated with a left ear of the patient to present a second set of one or more stimulation pulses to the patient. The first and second sets of stimulation pulses may be presented in any suitable order as described herein.

Figure 7:
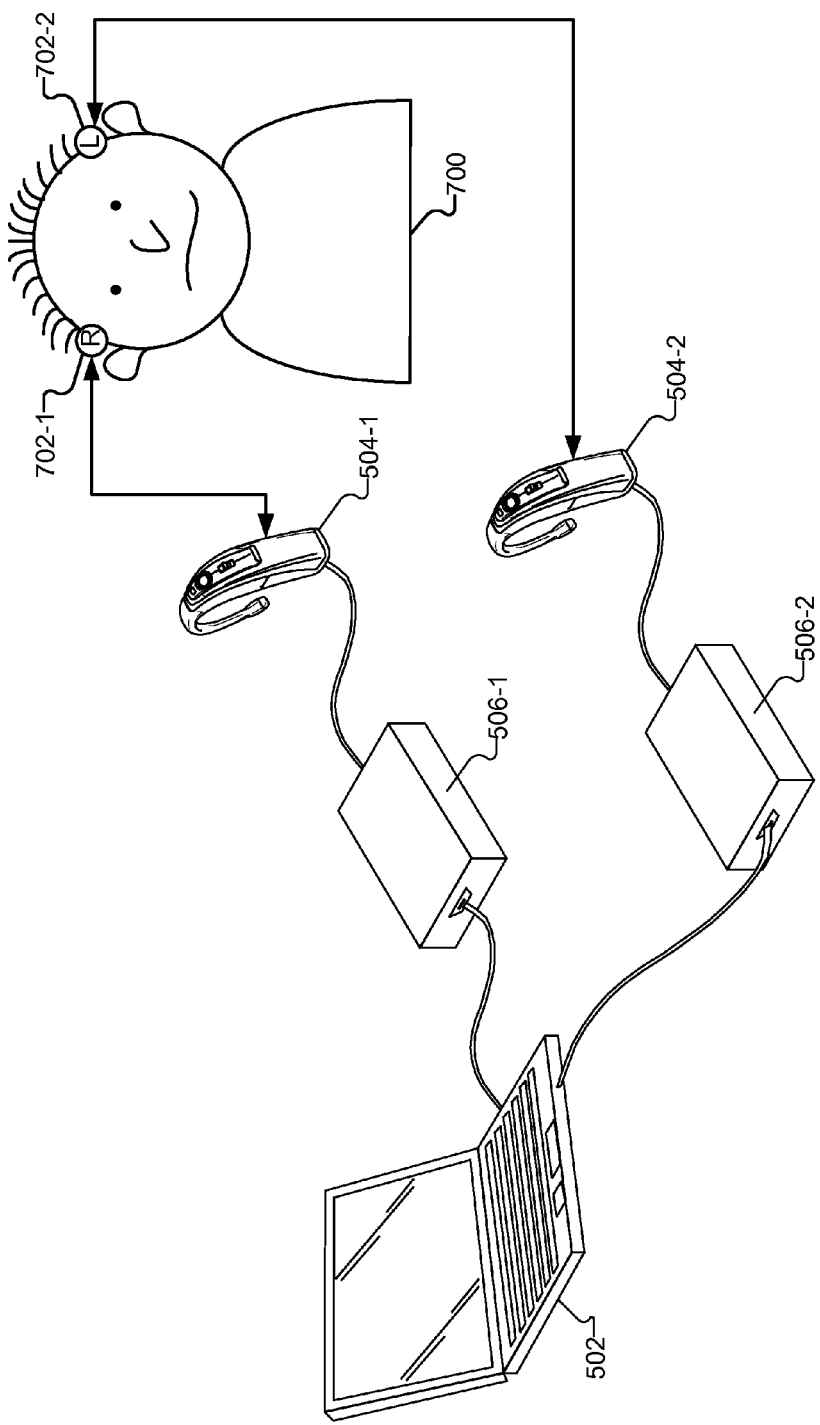
FIG. 7 shows an exemplary bilateral cochlear implant patient being fitted by the fitting components described in connection with FIG. 5 according to principles described herein.

To illustrate, FIG. 7 shows an exemplary bilateral cochlear implant patient 700 (or simply "patient 700") being fitted by the fitting components described in connection with FIG. 5. As shown in FIG. 7, patient 700 may have a first cochlear implant 702-1 associated with a first ear (e.g., the right ear) and a second cochlear implant 702-2 associated with a second ear (e.g., the left ear). Cochlear implants 702-1 and 702-2, collectively referred to herein as "cochlear implants 702", may be implanted in patient 700 using any suitable technique as may serve a particular implementation.

As shown, an audiologist may use fitting station 502, CPI 506-1, and first BTE unit 504-1 to fit first cochlear implant 702-1 to patient 700. The audiologist may likewise use fitting station 502, CPI 506-2, and second BTE unit 504-2 to fit second cochlear implant 702-2 to patient 700. For example, fitting station 502 may direct first cochlear implant 702-1 by way of BTE unit 504-1 to present the first set of one or more stimulation pulses to patient 700 and second cochlear implant 702-2 by way of BTE unit 504-2 to present the second set of one or more stimulation pulses to patient 700.

Returning to FIG. 6, in step 604, a first audible cue is presented during the presentation of each stimulation pulse included in the first set of one or more stimulation pulses. In step 606, a second audible cue is presented during the presentation of each stimulation pulse included in the second set of one or more stimulation pulses.

Figure 8:
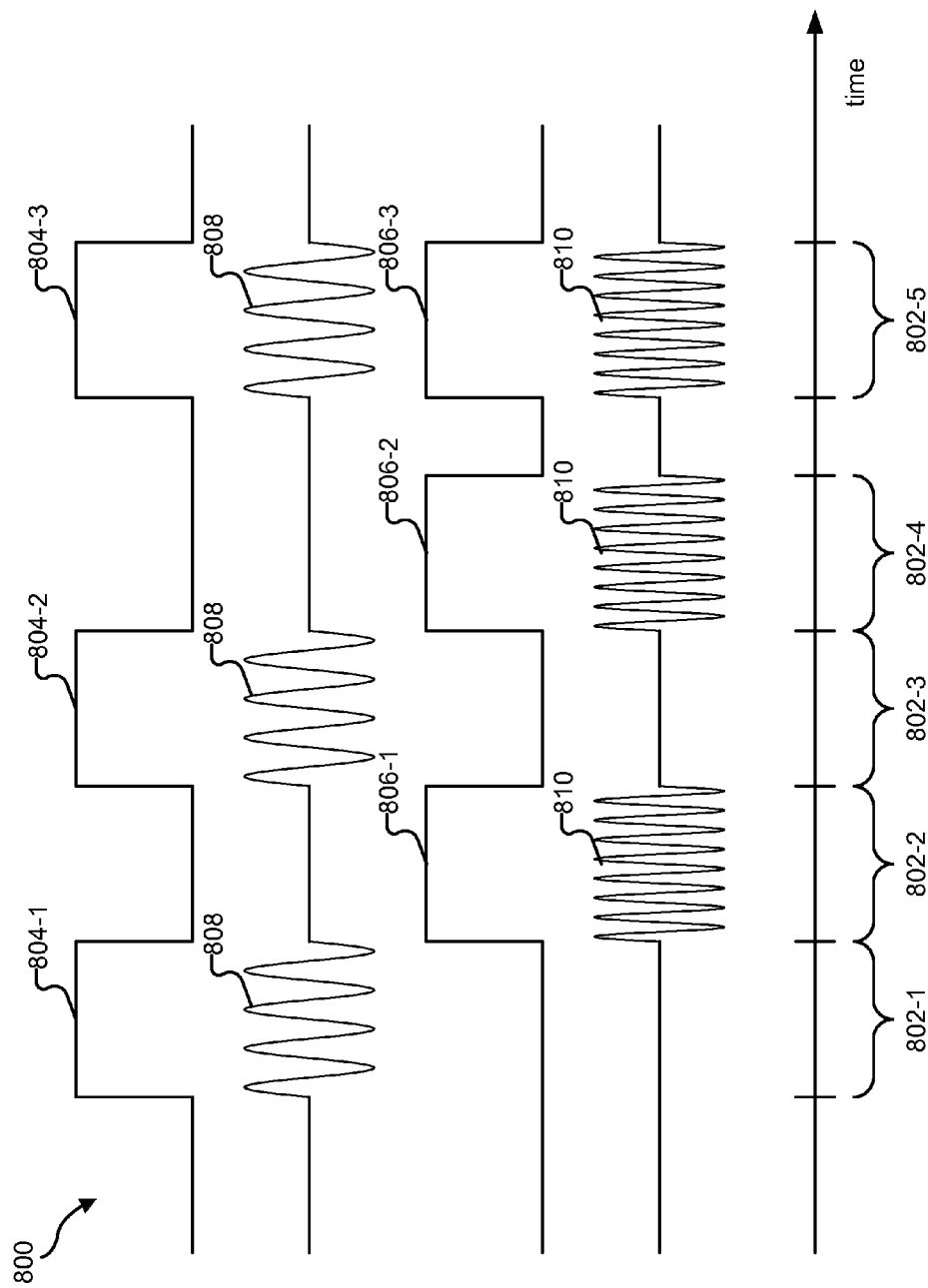
FIG. 8 shows a timing diagram that illustrates a presentation of first and second audible cues according to principles described herein.

FIG. 8 shows a timing diagram 800 that illustrates the presentation of the first and second audible cues in steps 604 and 606. As shown in timing diagram 800, various stimulation pulses and audible cues may be presented during different time periods 802 (e.g., time periods 802-1 through 802-5). For example, a first set of stimulation pulses 804-1 through 804-3 (collectively referred to herein as "stimulation pulses 804") may be presented by a first cochlear implant (e.g., cochlear implant 702-1) during time periods 802-1, 802-3, and 802-5, and a second set of stimulation pulses 806-1 through 806-3 (collectively referred to herein as "stimulation pulses 806") may be presented by a second cochlear implant (e.g., cochlear implant 702-2) during time periods 802-2, 802-4, and 802-5.

As shown in FIG. 8, fitting subsystem 202 may present a first audible cue 808 during a presentation of each stimulation pulse 804 included in the first set of stimulation pulses and a second audible cue 810 during a presentation of each stimulation pulse 806 included in the second set of stimulation pulses. First and second audible cues 808 and 810 may each have a distinct set of acoustic properties. For example, as illustrated in FIG. 8, first and second audible cues 808 and 810 may have distinct frequencies or pitches. In this manner, when a user hears first audible cue 808, he or she may know that a stimulation pulse (e.g., stimulation pulse 804-1) is being presented by the first cochlear implant. Likewise, when the user hears second audible cue 810, he or she may know that a stimulation pulse (e.g., stimulation pulse 806-1) is being presented by the second cochlear implant.

FIG. 8 also shows that stimulation pulses may be concurrently presented by the first and second cochlear implants. For example, stimulation pulses 804-3 and 806-3 may be presented by the first and second cochlear implants, respectively, during time period 802-5. First and second audible cues 808 and 810 may be also presented by fitting subsystem 202 during that time, as shown in FIG. 8. The combination of first and second audible cues 808 and 810 may be representative of the concurrent stimulation.

Figure 9:
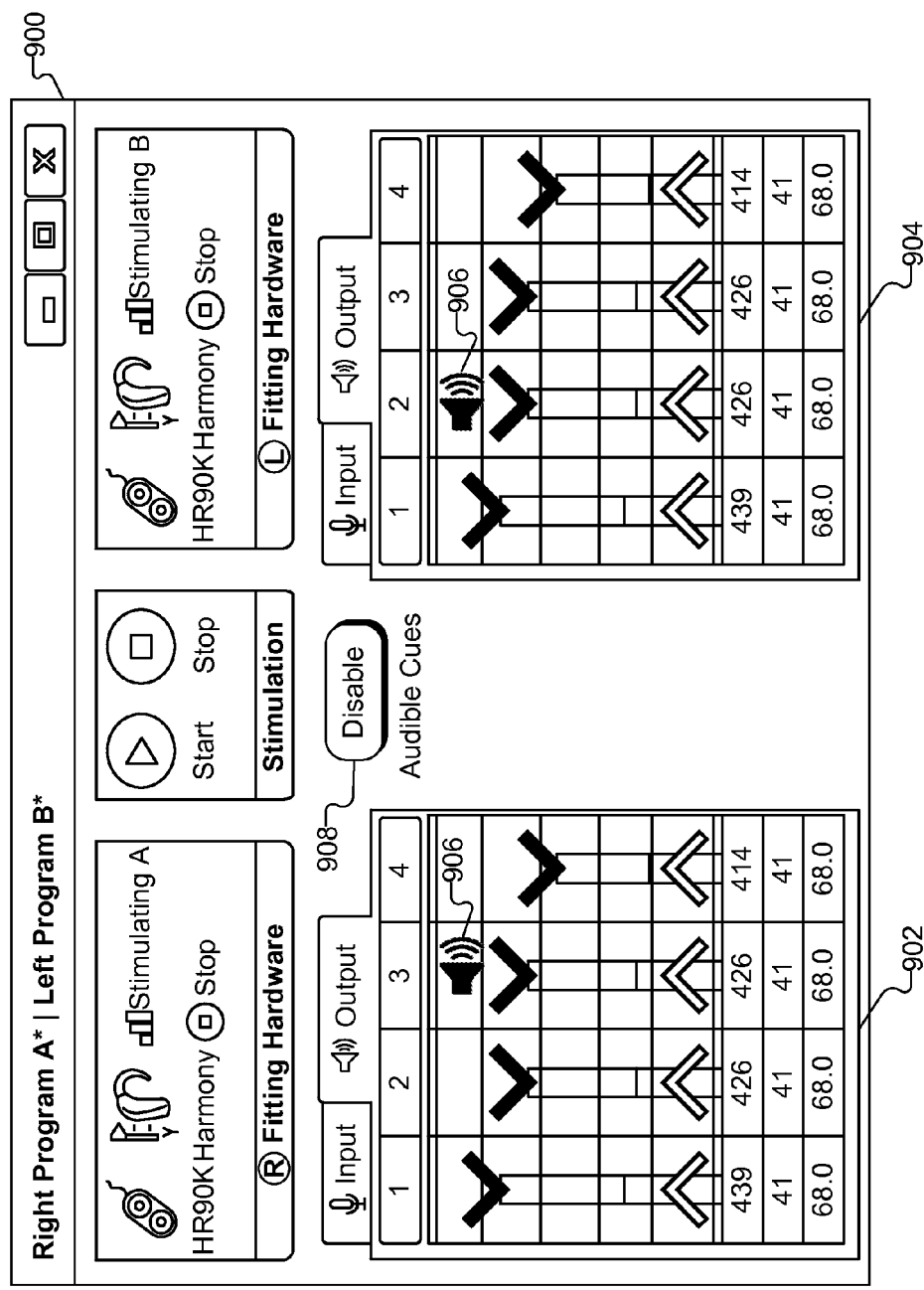
FIG. 9 illustrates an exemplary graphical user interface ("GUI") that may be used to fit a bilateral cochlear implant patient according to principles described herein.

FIG. 9 illustrates an exemplary graphical user interface ("GUI") 900 that may be provided for display by fitting subsystem 202 and that may be used to fit a bilateral cochlear implant patient. As shown in FIG. 9, GUI 900 may graphically indicate a presentation of the first and second sets of one or more stimulation pulses to the patient. For example, viewing portion 902 graphically indicates a presentation of stimulation pulses performed by a cochlear implant associated with the right ear of the patient and viewing portion 904 graphically indicates a presentation of stimulation pulses performed by a cochlear implant associated with the left ear of the patient. As shown in FIG. 9, one or more graphics 906 may be displayed within GUI 900 to indicate that audible cues are enabled. An option 908 may also be displayed within GUI 900 that may be selected by a user to disable the presentation of audible cues. Any other option associated with fitting a bilateral cochlear implant patient may be displayed within GUI 900 as may serve a particular implementation.

Figure 10:
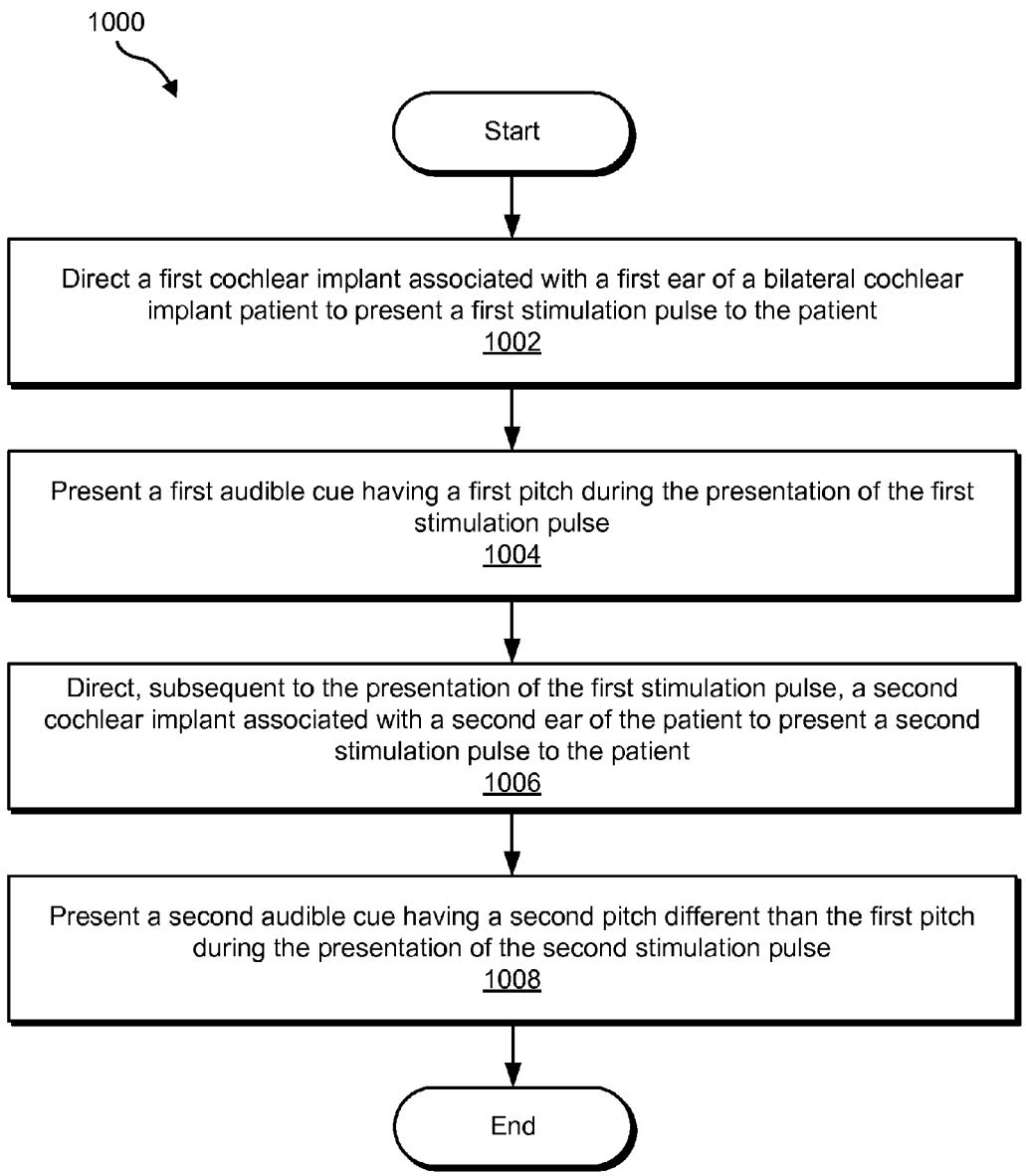
FIG. 10 illustrates another exemplary method of presenting audible cues to assist in fitting a bilateral cochlear implant patient according to principles described herein.

FIG. 10 illustrates another exemplary method 1000 of presenting audible cues to assist in fitting a bilateral cochlear implant patient. While FIG. 10 illustrates exemplary steps according to one embodiment, other embodiments may omit, add to, reorder, and/or modify any of the steps shown in FIG. 10. One or more of the steps shown in FIG. 10 may be performed by any component or combination of components of fitting subsystem 202 and/or fitting station 502.

In step 1002, a first cochlear implant associated with a first ear of a bilateral cochlear implant patient is directed to present a first stimulation pulse to the patient. Step 1002 may be performed in any of the ways described herein.

In step 1004, a first audible cue having a first pitch is presented during the presentation of the first stimulation pulse. Step 1004 may be performed in any of the ways described herein.

In step 1006, a second cochlear implant associated with a second ear of the patient is directed to present a second stimulation pulse to the patient subsequent to the presentation of the first stimulation pulse. Step 1006 may be performed in any of the ways described herein.

In step 1008, a second audible cue having a second pitch different than the first pitch is presented during the presentation of the second stimulation pulse. Step 1008 may be performed in any of the ways described herein.

In certain embodiments, one or more of the components and/or processes described herein may be implemented and/or performed by one or more appropriately configured computing devices. To this end, one or more of the systems and/or components described above may include or be implemented by any computer hardware and/or computer-implemented instructions (e.g., software) embodied on a non-transitory computer-readable medium configured to perform one or more of the processes described herein. In particular, system components may be implemented on one physical computing device or may be implemented on more than one physical computing device. Accordingly, system components may include any number of computing devices, and may employ any of a number of computer operating systems.

In certain embodiments, one or more of the processes described herein may be implemented at least in part as instructions executable by one or more computing devices. In general, a processor (e.g., a microprocessor) receives instructions, from a tangible computer-readable medium, (e.g., a memory, etc.), and executes those instructions, thereby performing one or more processes, including one or more of the processes described herein. Such instructions may be stored and/or transmitted using any of a variety of known non-transitory computer-readable media.

A non-transitory computer-readable medium (also referred to as a processor-readable medium) includes any non-transitory medium that participates in providing data (e.g., instructions) that may be read by a computer (e.g., by a processor of a computer). Such a non-transitory medium may take many forms, including, but not limited to, non-volatile media and/or volatile media. Non-volatile media may include, for example, optical or magnetic disks and other persistent memory. Volatile media may include, for example, dynamic random access memory ("DRAM"), which typically constitutes a main memory. Common forms of non-transitory computer-readable media include, for example, a floppy disk, flexible disk, hard disk, magnetic tape, any other magnetic medium, a CD-ROM, DVD, any other optical medium, a RAM, a PROM, an EPROM, a FLASH-EEPROM, any other memory chip or cartridge, or any other non-transitory medium from which a computer can read.

Figure 11:
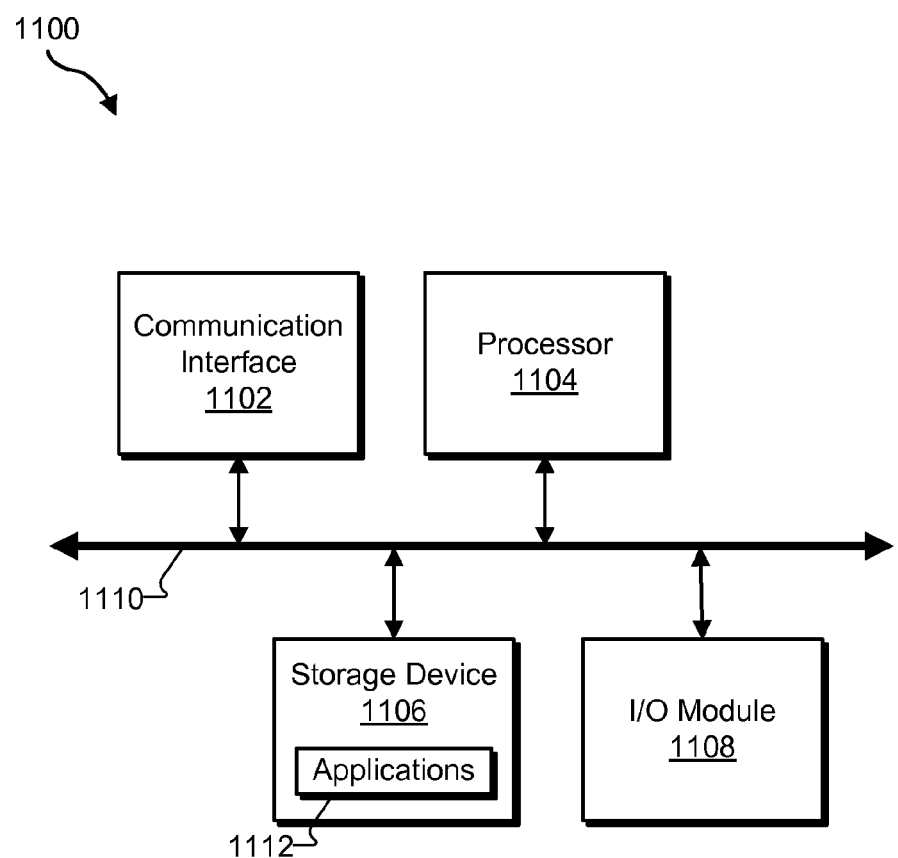
FIG. 11 illustrates an exemplary computing device according to principles described herein.

FIG. 11 illustrates an exemplary computing device 1100 that may be configured to perform one or more of the processes described herein. As shown in FIG. 11, computing device 1100 may include a communication interface 1102, a processor 1104, a storage device 1106, and an input/output ("I/O") module 1108 communicatively connected via a communication infrastructure 1110. While an exemplary computing device 1100 is shown in FIG. 11, the components illustrated in FIG. 11 are not intended to be limiting. Additional or alternative components may be used in other embodiments. Components of computing device 1100 shown in FIG. 11 will now be described in additional detail.

Communication interface 1102 may be configured to communicate with one or more computing devices. Examples of communication interface 1102 include, without limitation, a wired network interface (such as a network interface card), a wireless network interface (such as a wireless network interface card), a modem, and any other suitable interface. Communication interface 1102 may additionally or alternatively provide such a connection through, for example, a local area network (such as an Ethernet network), a personal area network, a telephone or cable network, a satellite data connection, a dedicated URL, or any other suitable connection. Communication interface 1102 may be configured to interface with any suitable communication media, protocols, and formats, including any of those mentioned above.

Processor 1104 generally represents any type or form of processing unit capable of processing data or interpreting, executing, and/or directing execution of one or more of the instructions, processes, and/or operations described herein. Processor 1104 may direct execution of operations in accordance with one or more applications 1112 or other computer-executable instructions such as may be stored in storage device 1106 or another non-transitory computer-readable medium.

Storage device 1106 may include one or more data storage media, devices, or configurations and may employ any type, form, and combination of data storage media and/or device. For example, storage device 1106 may include, but is not limited to, a hard drive, network drive, flash drive, magnetic disc, optical disc, random access memory ("RAM"), dynamic RAM ("DRAM"), other non-volatile and/or volatile data storage units, or a combination or sub-combination thereof. Electronic data, including data described herein, may be temporarily and/or permanently stored in storage device 1106. For example, data representative of one or more executable applications 1112 (which may include, but are not limited to, one or more of the software applications described herein) configured to direct processor 1104 to perform any of the operations described herein may be stored within storage device 1106. In some examples, data may be arranged in one or more databases residing within storage device 1106.

I/O module 1108 may be configured to receive user input and provide user output and may include any hardware, firmware, software, or combination thereof supportive of input and output capabilities. For example, I/O module 1108 may include hardware and/or software for capturing user input, including, but not limited to, a keyboard or keypad, a touch screen component (e.g., touch screen display), a receiver (e.g., an RF or infrared receiver), and/or one or more input buttons.

I/O module 1108 may include one or more devices for presenting output to a user, including, but not limited to, a graphics engine, a display (e.g., a display screen, one or more output drivers (e.g., display drivers), one or more audio speakers, and one or more audio drivers. In certain embodiments, I/O module 1108 is configured to provide graphical data to a display for presentation to a user. The graphical data may be representative of one or more graphical user interfaces and/or any other graphical content as may serve a particular implementation.

In some examples, any of the facilities described herein may be implemented by or within one or more components of computing device 1100. For example, one or more applications 1112 residing within storage device 1106 may be configured to direct processor 1104 to perform one or more processes or functions associated with communication facility 302, user interface facility 304, fitting facility 306, audio presentation facility 308, communication facility 402, and/or processing facility 404. Likewise, storage facility 310 and/or storage facility 406 may be implemented by or within storage device 1106.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A method comprising:
   directing, by a fitting subsystem, a first cochlear implant associated with a right ear of a bilateral cochlear implant patient to present a first set of one or more stimulation pulses to the patient and a second cochlear implant associated with a left ear of the patient to present a second set of one or more stimulation pulses to the patient;
   generating and presenting, by the fitting subsystem, a first audible cue to a clinician during the presentation of each stimulation pulse included in the first set of one or more stimulation pulses, the first audible cue comprising a first distinct set of acoustic properties configured to acoustically indicate that the first cochlear implant associated with the right ear of the bilateral cochlear implant patient is a source of the first set of one or more stimulation pulses; and
   generating and presenting, by the fitting subsystem, a second audible cue to the clinician during the presentation of each stimulation pulse included in the second set of one or more stimulation pulses, the second audible cue comprising a second distinct set of acoustic properties configured to acoustically indicate that the second cochlear implant associated with the left ear of the bilateral cochlear implant patient is a source of the second set of one or more stimulation pulses.

2. The method of claim 1, wherein
   the presentation of the first audible cue to the clinician is synchronized with the presentation of each stimulation pulse included in the first set of one or more stimulation pulses; and
   the presentation of the second audible cue to the clinician is synchronized with the presentation of each stimulation pulse included in the second set of one or more stimulation pulses.

3. The method of claim 1, wherein the first audible cue has a first pitch and the second audible cue has a second pitch different than the first pitch.

4. The method of claim 1, wherein the first audible cue has a first volume level and the second audible cue has a second volume level different than the first volume level.

5. The method of claim 1, wherein a stimulation pulse included in the first set of one or more stimulation pulses and a stimulation pulse included in the second set of one or more stimulation pulses are presented concurrently to the patient by the first and second cochlear implants, and wherein the presentation of the first audible cue and the second audible cue during the concurrent presentation of the of the stimulation pulses results in a mixed audible cue configured to be acoustically representative of the concurrent presentation of the stimulation pulses.

6. The method of claim 1, further comprising providing, by the fitting subsystem, a graphical user interface configured to graphically indicate the presentation of the first and second sets of one or more stimulation pulses to the patient.

7. The method of claim 6, further comprising providing a selectable option within the graphical user interface to selectively disable the presentation of the first and second audible cues.

8. The method of claim 1, further comprising:
   dynamically adjusting, by the fitting subsystem, one or more acoustic properties of the first audible cue in accordance with a change in stimulation level of one or more stimulation pulses included in the first set of one or more stimulation pulses; and
   dynamically adjusting, by the fitting subsystem, one or more of the acoustic properties of the second audible cue in accordance with a change in stimulation level of one or more stimulation pulses included in the second set of one or more stimulation pulses.

9. The method of claim 1, embodied as computer-executable instructions on at least one non-transitory computer-readable medium.

10. The method of claim 1, embodied as computer-executable instructions on at least one non-transitory computer-readable medium.

11. A method comprising:
    directing, by a fitting subsystem, a first cochlear implant associated with a first ear of a bilateral cochlear implant patient to present a first stimulation pulse to the patient;
    generating and presenting to a clinician, by the fitting subsystem, a first audible cue having a first pitch during the presentation of the first stimulation pulse, the first audible cue comprising a first distinct set of acoustic properties configured to acoustically indicate that the first cochlear implant associated with the right ear of the bilateral cochlear implant patient is a source of the first stimulation pulse;
    directing, by the fitting subsystem subsequent to the presentation of the first stimulation pulse, a second cochlear implant associated with a second ear of the patient to present a second stimulation pulse to the patient; and
    generating and presenting to the clinician, by the fitting subsystem, a second audible cue having a second pitch different than the first pitch during the presentation of the second stimulation pulse, the second audible cue comprising a second distinct set of acoustic properties configured to acoustically indicate that the second cochlear implant associated with the left ear of the bilateral cochlear implant patient is a source of the second stimulation pulse.

12. The method of claim 11, further comprising:
    directing, by the fitting subsystem, the first cochlear implant to present a third stimulation pulse to the patient;
    directing, by the fitting subsystem, the second cochlear implant to present a fourth stimulation pulse to the patient concurrently with the presentation of the third stimulation pulse; and
    generating and presenting to the clinician, by the fitting subsystem, a third audible cue having a third pitch different than the first and second pitches during the concurrent presentation of the third and fourth stimulation pulses.

13. The method of claim 12, wherein the third audible cue comprises a mixed combination of the first and second audible cues.

14. The method of claim 11, wherein
    the presentation to the clinician of the first audible cue is synchronized with the presentation of the first stimulation pulse; and the presentation to the clinician of the second audible cue is synchronized with the presentation of the second stimulation pulse.

15. The method of claim 11, further comprising providing, by the fitting subsystem, a graphical user interface configured to graphically indicate the presentation of the first and second stimulation pulses to the patient.

16. The method of claim 15, further comprising providing a selectable option within the graphical user interface to selectively disable the presentation of the first and second audible cues to the clinician.

17. A system comprising:
a fitting facility configured to direct a first cochlear implant associated with a right ear of a bilateral cochlear implant patient to present a first set of one or more stimulation pulses to the patient and a second cochlear implant associated with a left ear of the patient to present a second set of one or more stimulation pulses to the patient; and
an audio presentation facility communicatively coupled to the fitting facility and configured to
generate and present a first audible cue to a clinician during the presentation of each stimulation pulse included in the first set of one or more stimulation pulses, the first audible cue comprising a first distinct set of acoustic properties configured to acoustically indicate that the first cochlear implant associated with the right ear of the bilateral cochlear implant patient is a source of the first set of one or more stimulation pulses, and
generate and present a second audible cue to the clinician having one or more different acoustic properties than the first audible cue during the presentation of each stimulation pulse included in the second set of one or more stimulation pulses, the second audible cue comprising a second distinct set of acoustic properties configured to acoustically indicate that the second cochlear implant associated with the left ear of the bilateral cochlear implant patient is a source of the second set of one or more stimulation pulses.

18. The system of claim 17, wherein the audio presentation facility is configured to concurrently generate and present the first and second audible cues to the clinician to indicate a concurrent presentation of a stimulation pulse included in the first set of one or more stimulation pulses and a stimulation pulse included in the second set of one or more stimulation pulses.

19. The system of claim 17, wherein the first audible cue has a first pitch and the second audible cue has a second pitch different than the first pitch.

20. The system of claim 17, further comprising a user interface facility communicatively coupled to the fitting facility and configured to provide a graphical user interface configured to graphically indicate the presentation of the first and second sets of one or more stimulation pulses to the patient.

* * * * *